United States Patent
Li et al.

(10) Patent No.: US 9,261,429 B2
(45) Date of Patent: Feb. 16, 2016

(54) PRISM-COUPLING SYSTEMS AND METHODS FOR CHARACTERIZING LARGE DEPTH-OF-LAYER WAVEGUIDES

(71) Applicant: Corning Incorporated, Corning, NY (US)

(72) Inventors: Shenping Li, Painted Post, NY (US); Rostislav Vatchev Roussev, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 14/707,431

(22) Filed: May 8, 2015

(65) Prior Publication Data

US 2015/0338308 A1   Nov. 26, 2015

Related U.S. Application Data

(60) Provisional application No. 62/001,116, filed on May 21, 2014.

(51) Int. Cl.
*G01B 11/16* (2006.01)
*G01M 11/00* (2006.01)
(Continued)

(52) U.S. Cl.
CPC .......... *G01M 11/3181* (2013.01); *G01B 11/22* (2013.01); *G01J 4/04* (2013.01);
(Continued)

(58) Field of Classification Search
CPC .... G01B 11/16; G01B 11/22; G01M 11/3181

USPC ........................................................ 356/32
See application file for complete search history.

(56) References Cited

U.S. PATENT DOCUMENTS 4,152,045 A   5/1979   Hammer
4,655,589 A * 4/1987   Cestaro .................. G01L 1/241
                                                          356/35

(Continued)

FOREIGN PATENT DOCUMENTS

CN   101726471 A   6/2010
CN   101592537 B   12/2012
(Continued)

OTHER PUBLICATIONS

Chen; "Measurement error in prism coupling method and refractive Index profile reconstruction in ion-exchanged waveguides"; Measurements, 44 (2011) 1080-1083.
(Continued)

*Primary Examiner* — Roy M Punnoose
(74) *Attorney, Agent, or Firm* — Timothy M. Schaeberle (57) ABSTRACT

Prism-coupling systems and methods for characterizing large depth-of-layer waveguides are disclosed. The systems and methods utilize a coupling prism having a coupling angle $\alpha$ having a maximum coupling angle $\alpha_{max}$ at which total internal reflection occurs. The prism angle $\alpha$ is in the range $0.81\alpha_{max} \leq \alpha \leq 0.99\alpha_{max}$. This configuration causes the more spaced-apart lower-order mode lines to move closer together and the more tightly spaced higher-order mode lines to separate. The adjusted mode-line spacing allows for proper sampling at the detector of the otherwise tightly spaced mode lines. The mode-line spacings of the detected mode spectra are then corrected via post-processing. The corrected mode spectra are then processed to obtain at least one characteristic of the waveguide.

20 Claims, 8 Drawing Sheets

(51) Int. Cl.
  *G01L 1/24* (2006.01)
  *G01B 11/22* (2006.01)
  *G01J 4/04* (2006.01)
  *G01N 21/41* (2006.01)
  *G01N 21/84* (2006.01)
  *G01N 21/23* (2006.01)
  *G02B 5/04* (2006.01)
  *G01J 4/00* (2006.01)

(52) U.S. Cl.
  CPC .................. *G01L 1/24* (2013.01); *G01N 21/41* (2013.01); *G01N 21/8422* (2013.01); *G01J 2004/005* (2013.01); *G01N 21/23* (2013.01); *G01N 2021/4126* (2013.01); *G02B 5/04* (2013.01)

(56) References Cited

U.S. PATENT DOCUMENTS

| | | | | |
|---|---|---|---|---|
| 5,164,589 | A * | 11/1992 | Sjodin | G01N 21/552 250/227.24 |
| 6,917,730 | B2 | 7/2005 | Ghiron et al. | |
| 8,957,374 | B2 * | 2/2015 | Liu | G01N 21/23 250/338.1 |
| 2014/0092377 | A1 * | 4/2014 | Liu | G01N 21/23 356/51 |

FOREIGN PATENT DOCUMENTS

| | | |
|---|---|---|
| JP | 11281501 A | 10/1999 |
| WO | 2009063756 A1 | 5/2009 |
| WO | 2012128184 A1 | 9/2012 |

OTHER PUBLICATIONS

Tien et al; "Modes of propagating light waves in thin deposited semiconductor films"; Applied Physics Letters; May 1, 1969; vol. 14, No. 9, pp. 291-294.

PCT/US15/031722 PCT Search Report dated Aug. 21, 2015.

Ay et al.; "Prism coupling technique investigation of elasto-optical properties of thin polymer films"; Journal of Applied Physics, vol. 96, No. 12 (2004); pp. 7147-7153.

Ulrich et al.; "Measurement of Thin Film Parameters with a Prism Coupler"; Applied Optics, vol. 12, No. 12 (Dec. 1973); pp. 2901-2908.

Valles-Villarreal et al.; "Stress in Copper Ion-Exchanged Glass Waveguides"; Journal of Lightwave Technology, vol. 17, No. 4 (Apr. 1999); pp. 606-612.

White et al.; "Optical waveguide refractive index profiles determined from measurement of mode indices: a simple analysis"; Applied Optics, vol. 15, No. 1 (Jan. 1976); pp. 151-155.

* cited by examiner

PRISM-COUPLING SYSTEMS AND METHODS FOR CHARACTERIZING LARGE DEPTH-OF-LAYER WAVEGUIDES

This application claims the benefit of priority under 35 U.S.C. §119 of U.S. Provisional Application Ser. No. 62/001,116, filed on May 21, 2014, the content of which is relied upon and incorporated herein by reference in its entirety.

FIELD

The present disclosure relates to prism-coupling systems and methods for characterizing waveguides, and in particular relates to systems and methods for characterizing large depth-of-layer waveguides.

The entire disclosure of any publication or patent document mentioned herein is incorporated by reference, including U.S. patent application Ser. No. 13/463,322, entitled "Systems and methods for measuring the stress profile of ion-exchanged glass," and in U.S. Patent Application Publication No 2014/0092377, entitled "Systems and methods for measuring birefringence in glass and glass-ceramics," and U.S. Provisional Patent Application Ser. No. 61/897,546, entitled "Apparatus and methods for measurement of mode spectra of index profiles containing a steep region." (hereinafter, the '546 application).

BACKGROUND

Prism-coupling techniques can be used to measure the spectrum of guided modes of a planar optical waveguide to characterize the waveguide properties, e.g., to measure the refractive index and stress profiles. This technique has been used to measure the stress and the depth-of-layer (DOL) of different ion-exchanged (IOX) glasses.

Certain types of IOX glasses are actual dual IOX (DIOX) glasses formed by first and second diffusions that give rise to a two-segment profile. The first segment is adjacent the surface and has a relatively steep slope, while the second segment extends deeper into the substrate but has a relatively shallow slope. Such DIOX profiles are formed in certain types of chemically strengthened glasses and anti-microbial glasses.

Such two-segment profiles result in a relatively large spacing between low-order modes, which have a relatively high effective index, and a very small spacing between high-order modes, which have a relatively low effective index. This difference in mode spacing is further enhanced when a conventional coupling prism, which has an output-side angle α of about 60°, is used. For such a coupling prism, angular sensitivity of exit rays is higher for the low-order modes than for the high-order modes. The spacing between modes is of interest since the modes are detected by a photodetector (i.e., a digital camera). The resolution of the measurement is defined by the number of photodetector pixels between adjacent modes.

By way of example, consider a typical refractive index profile of a DIOX glass formed using $Ag^+$ (shallow) and $K^+$ (deep) diffusions. The steep, shallow $Ag^+$ IOX region can have an index variation of about 0.06 and a depth of about 3 µm from the glass surface. The shallower but deeper $K^+$ IOX region can have a substantially smaller index variation of only about 0.01 and a depth of about 90 µm from the glass surface. The spacing between the lowest-order two (TE or TM) modes at the photodetector can be many hundreds of pixels, while the spacing between the highest-order two modes may be only a few pixels.

This distribution of the modes over the photodetector pixels is problematic when precise measurements of the deeper segment of the DIOX profile are sought because the high-order modes that travel in the deeper segment are undersampled. If the DOL is large enough, it becomes impossible to adequately resolve the spectral lines of high-order modes, and as a result the DIOX profile cannot be precisely measured.

One option for obtaining the required measurement resolution is to have a larger photodetector with more pixels, which in some cases may also require a larger-aperture optical system. However, such photodetectors and larger-aperture optical systems add substantial cost and complexity to the measurement system.

SUMMARY

Prism-coupling systems and methods for characterizing large depth-of-layer waveguides, such as those formed in DIOX glass samples, are disclosed. The systems and methods utilize a coupling prism having a coupling angle α with a maximum coupling angle $\alpha_{max}$ at which total internal reflection occurs. The prism angle α is in the range $0.81\alpha_{max} \leq \alpha \leq 0.99\alpha_{max}$. This configuration causes a favorable adjustment of the mode spectrum, wherein the more tightly spaced higher-order mode lines are better separated in terms of exit angle from the prism. A detector detects the adjusted mode spectrum, whose adjusted mode-line spacing allows for proper sampling of the otherwise tightly spaced mode lines of the higher-order modes, while making more efficient use of the detector space for the originally more widely separated mode lines of the lower-order modes. The mode-line spacings of the detected mode spectrum are then re-adjusted (corrected) via post-processing. The re-re-adjusted (corrected) mode spectrum is then processed to obtain at least one characteristic of the waveguide. The method can be applied to both TM and TE mode spectra to obtain a measurement of the birefringence profile and thus a measure of the stress profile of the waveguide.

An aspect of the disclosure is a measurement system for measuring at least one mode spectrum of a waveguide formed in a top surface of a substrate and having a depth-of-layer (DOL) of greater than 50 microns. The measurement system includes: a coupling prism having an input surface, an output surface and a coupling surface, a refractive index $n_p$, and a prism angle α between the output surface and the coupling surface, and wherein the coupling surface interfaces with the waveguide at the substrate top surface, thereby defining a substrate-prism interface; a light source system configured to illuminate the substrate-prism interface through the input surface of the prism, thereby forming reflected light that includes mode lines of the at least one mode spectrum having a first size, wherein the reflected light exits the output surface of the coupling prism; a photodetector system having a detector and arranged to receive the reflected light from the coupling prism and detect the at least one mode spectrum on the detector; and a controller configured to process the detected at least one mode spectrum to correct a distortion of the mode lines caused by refraction of the reflected light at the output surface of the coupling prism to a corrected mode spectrum having a second size; and wherein the coupling prism has a maximum prism angle $\alpha_{max}$ equal to the critical angle at greater than which the reflected light is totally internally reflected at the output surface of the prism, the prism angle α is in the range $0.81\alpha_{max} \leq \alpha \leq 0.99\alpha_{max}$, and the first size is substantially the same as the second size.

Another aspect of the disclosure is a method of measuring mode spectra of a waveguide formed in a top surface of a substrate having a DOL greater than 50 microns. The method includes: interfacing a coupling prism with the substrate to form a substrate-prism interface, the coupling prism having a coupling prism angle defined by an output surface and that is in the range $0.81\alpha_{max} \leq \alpha \leq 0.99\alpha_{max}$, wherein $\alpha_{max}$ defines a maximum coupling prism angle associated with total internal reflection occurring within the coupling prism; directing light through the coupling prism to the substrate-prism interface to form reflected light that includes mode lines of at least one mode spectrum of the waveguide, wherein the reflected light exits the output surface of the coupling prism; detecting the mode lines of the at least one mode spectrum of the reflected light that exits the coupling prism, wherein the mode lines have an adjusted mode-line spacing due to refraction of the reflected light at the output surface of the coupling prism; and correcting the adjusted mode-line spacing after said detecting.

Another aspect of the disclosure is a method of measuring mode spectra of a waveguide formed in a top surface of a substrate by double ion diffusion to a DOL greater than 50 microns. The method includes: interfacing a coupling prism with the waveguide, the coupling prism having an input surface, an output surface, a coupling surface that interfaces the top surface to define a substrate-prism interface, the coupling prism having a coupling prism angle $\alpha$ defined by the coupling surface and the output surface, and a maximum prism angle $\alpha_{max}$ that corresponds to a total internal reflection angle at the output surface, wherein the coupling prism angle is in the range $0.81\alpha_{max} \leq \alpha \leq 0.99\alpha_{max}$; directing light through the input surface to the substrate-prism interface, thereby forming reflected light that includes mode lines of the mode spectra, wherein the reflected light exits the coupling prism at the output surface and is made incident upon a detector; detecting with the detector the mode lines of the mode spectra, wherein the mode lines have an adjusted mode spacing due to refraction of the reflected light at the output surface of the coupling prism; and after said detecting, correcting the adjustment in the mode-line spacing.

Additional features and advantages are set forth in the Detailed Description that follows, and in part will be readily apparent to those skilled in the art from the description or recognized by practicing the embodiments as described in the written description and claims hereof, as well as the appended drawings. It is to be understood that both the foregoing general description and the following Detailed Description are merely exemplary and are intended to provide an overview or framework to understand the nature and character of the claims.

BRIEF DESCRIPTION OF THE DRAWINGS

The accompanying drawings are included to provide a further understanding and are incorporated in and constitute a part of this specification. The drawings illustrate one or more embodiment(s) and together with the Detailed Description serve to explain principles and operation of the various embodiments. As such, the disclosure will become more fully understood from the following Detailed Description, taken in conjunction with the accompanying Figures, in which.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

Cartesian coordinates are shown in some of the Figures for the sake of reference and are not intended to be limiting as to direction or orientation.

The abbreviation RIU stands for "refractive index units."

The discussion below refers to lower-order modes and higher-order modes of the waveguide formed by the IOX process. The modes are ordered by the number of zeroes (nodes) in the depth distribution of the electric field amplitude. The lowest-order mode (labeled $TM_0$ for transverse-magnetic modes and $TE_0$ for transverse-electric modes) has no zeroes in the distribution, and has the highest effective index. The second mode ($TM_1$ or $TE_1$), has one node in the depth distribution of its electric field amplitude, and the second-highest effective index, and so on. The highest-order guided mode for each of the two polarization states supported by the waveguide has the most zeroes in the depth distribution of electric field amplitude, and the lowest effective index among the modes of that polarization state.

In many examples pertaining to chemically strengthened glasses with large DOL, the strengthening ion (such as $K^+$ in the ion exchange $K^+$ for $Na^+$), the effective index of the highest-order mode may be only slightly higher than the substrate or bulk glass index, and the effective index of the lowest-order (fundamental) mode may be only slightly lower than the maximum value of the material refractive index anywhere inside the waveguide (often occurring at the glass surface).

Thus, the terms "higher-order mode" and "lower-order mode" as used herein are somewhat relative in that we may define for the sake of convenience a certain number of the lowest-order modes to collectively be "low-order modes" and the remaining modes that are higher to constitute "higher-order modes." Consequently, the particular distinction used to differentiate between the modes or to refer to the modes as being in different groups is for ease of description and is not intended to be limiting.

Figure 1A:
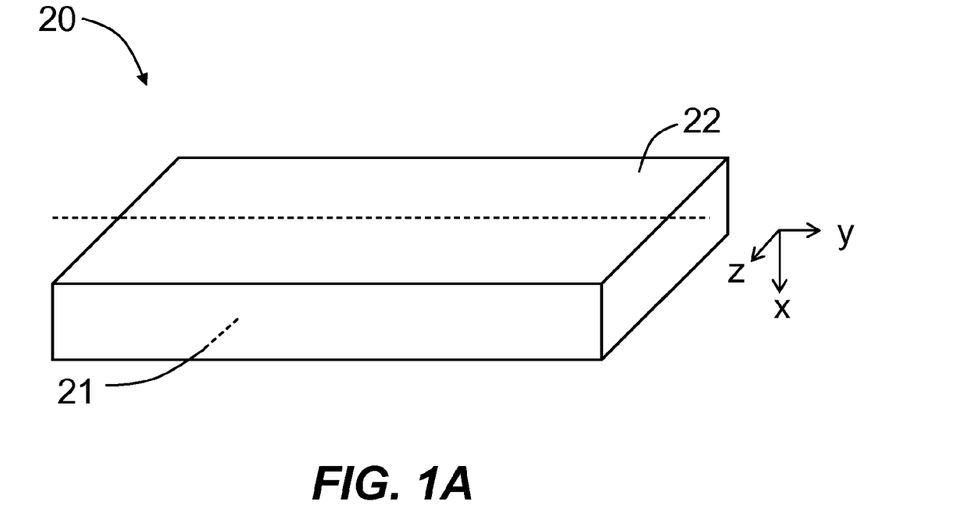
FIG. 1A is an elevated view of an example DIOX glass substrate in the form of a planar substrate.
Figure 1B:
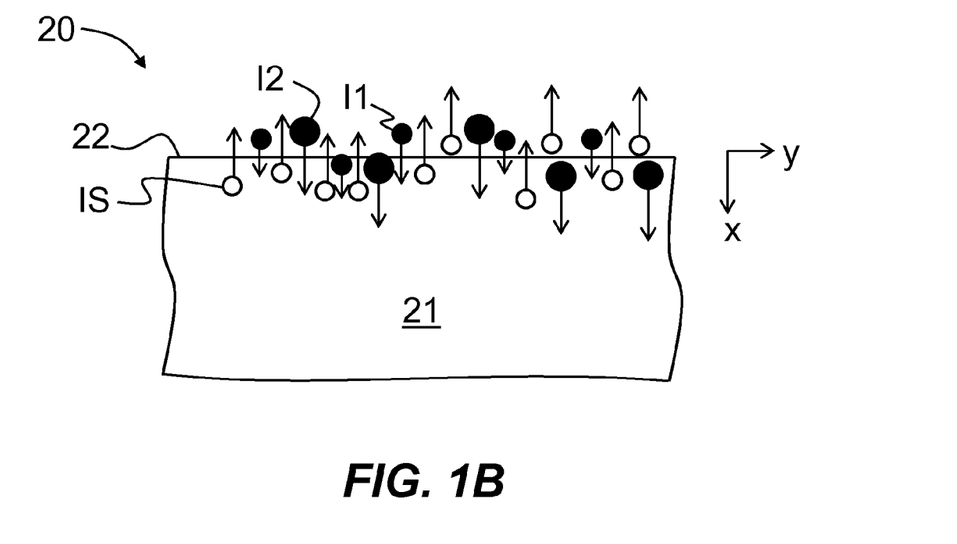
FIG. 1B is a close-up cross-sectional view of the DIOX substrate of FIG. 1A as taken in the x-y plane and that illustrates the double ion-exchange process that takes place across the substrate surface and into the body of the substrate.

FIG. 1A is an elevated view an example glass substrate in the form of a planar ion-exchanged substrate 20 that has a body 21 and a (top) surface 22, wherein the body has a base (bulk) refractive index $n_s$ and a surface refractive index $n_0$. FIG. 1B is a close-up cross-sectional view of ion-exchanged substrate 20 as taken in the x-y plane and illustrates an example double ion-exchange (DIOX) process that takes place across surface 22 and into body 21 in the x-direction.

Figure 1C:
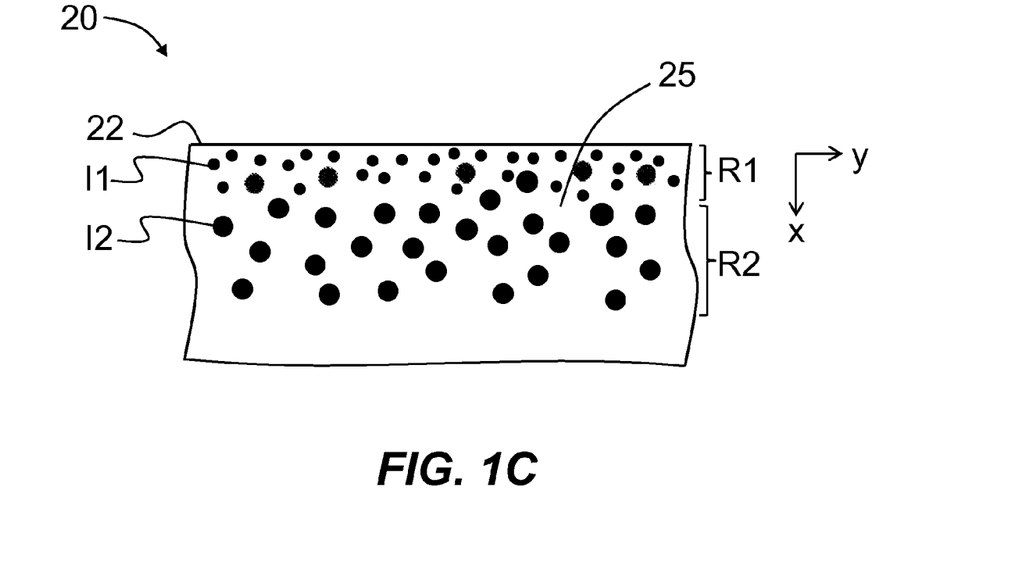
FIG. 1C schematically illustrates the result of the DIOX process that forms the DIOX substrate.

FIG. 1C schematically illustrates the result of the double ion-exchange process that forms (double) ion-exchanged substrate 20. The ion-exchanged substrate 20 includes substrate ions IS in body 21 that exchange for first ions I1 and second ions I2. The first and second ions I1 and I2 can be introduced into the glass body either sequentially or concurrently using known techniques. For example, second ions I2 can be $K^+$ ions introduced via a $KNO_3$ bath for strengthening, prior to introducing first ions I1 that can be $Ag^+$ ions introduced via a $AgNO_3$-containing bath to add the anti-microbial property adjacent surface 22. The circles in FIG. 1B that represent ions I1 and I2 are used for schematic illustration only, and their relative sizes do not necessarily represent any actual relationship between the sizes of the actual ions participating in the ion exchange.

In addition, ions I1 may be present in significant numbers in both regions R1 and R2 (see FIG. 2, introduced and discussed below) as may be ions of type I2. Even with a one-step ion-exchange process it is possible to observe the formation of two regions R1 and R2, with significant differences in the relative concentrations of ions I1 and I2. In an example, using an ion exchange of Na-containing glass in a bath containing a mixture of $KNO_3$ and $AgNO_3$, it is possible to obtain region R1 with significant concentrations of both $Ag^+$ and $K^+$, and region R2 also with significant concentrations of $Ag^+$ and $K^+$, but the relative concentration of $Ag^+$ with respect to $K^+$ may be significantly larger in region R1 than in region R2.

Figure 2:
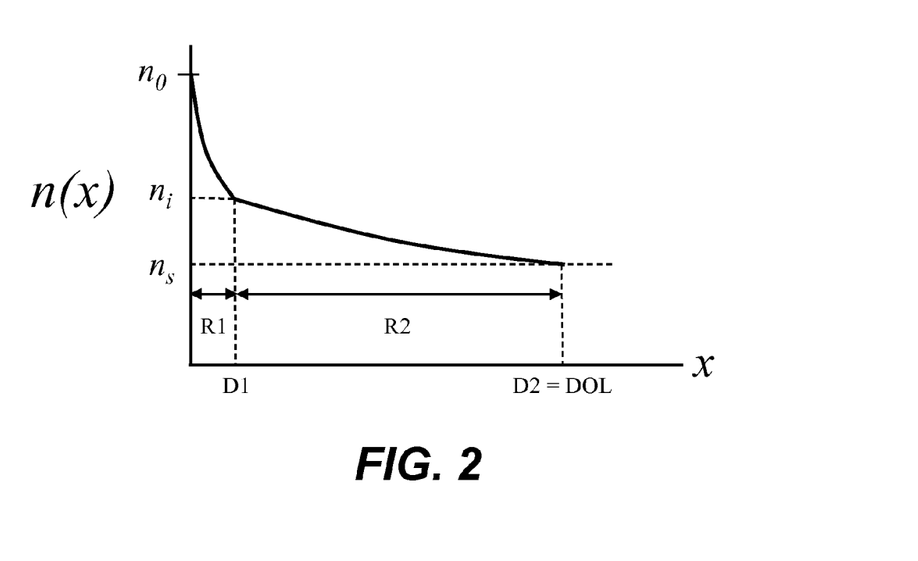
FIG. 2 is a representation of an example refractive index profile n(x) for each side of the DIOX substrate illustrated in FIG. 1C.

FIG. 2 is a representation of an example refractive index profile n(x) for ion-exchanged substrate 20 such as illustrated in FIG. 1C. The refractive index profile n(x) includes a first region R1 associated with the shallower ion-exchange (ions I1) and that has a depth D1 into body 21. The refractive index profile n(x) also includes a second region R2 associated with the deeper ion-exchange (ions I2) and that has a depth D2 that defines the depth-of-layer (DOL). In an example, DOL is at least 50 µm and further in an example can be as large as 150 µm. In another example DOL is in the range from 70 µm to 100 µm.

The deeper second region R2 may be produced in practice prior to the shallower region. The region R1 is adjacent substrate surface 22 and is relatively steep and shallow (e.g., D1 is a few microns), whereas region R2 is less steep and extends relatively deep into the substrate to the aforementioned depth D2. In an example, region R1 has a maximum refractive index $n_0$ at substrate surface 22 and steeply tapers off to an intermediate index $n_i$, while region R2 tapers more gradually from the intermediate index down to the substrate (bulk) refractive index $n_s$. It is emphasized here that other ion-exchanged processes can result in a steep and shallow near-surface refractive index change and that a double ion-exchange process is discussed here by way of illustration.

In an example, the methods disclosed herein employ optical measurements of ion-exchanged substrate 20 using a prism-coupling system as described below that includes a specialized coupling prism. Such systems that employ a conventional coupling prism are generally known in the art, and example systems suitable for use in carrying out the methods of the present disclosure with the modifications of the coupling prism as set forth below are described in the above-identified U.S. patent applications.

Prism-Coupling System

Figure 3A:
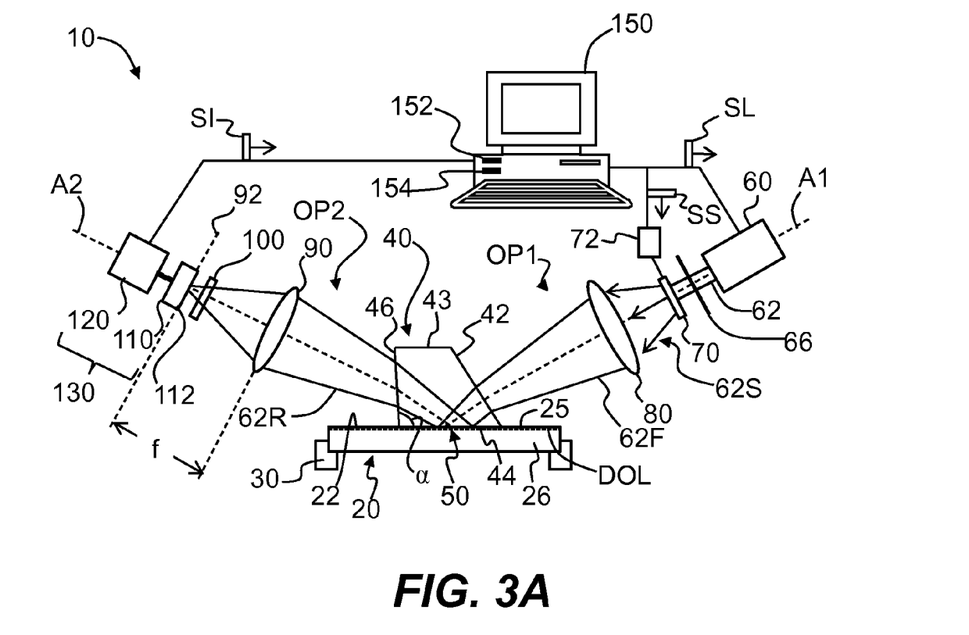
FIG. 3A is a schematic diagram of an example prism-coupling system according to the disclosure.
Figure 3B:
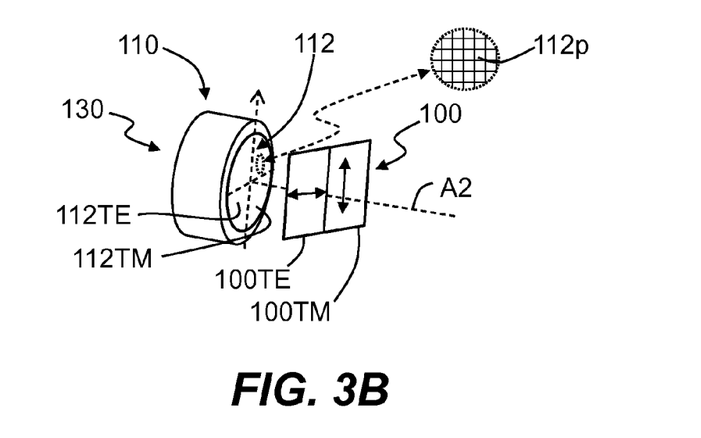
FIG. 3B is a close-up view of the photodetector system of the prism-coupling system of FIG. 3A.

FIG. 3A is a schematic diagram of an example prism-coupling system ("system") 10 suitable for carrying out the methods of measuring the TE and TM mode spectra for ion-exchanged substrate 20 having a refractive profile n(x). FIG. 3B is a close-up view of the photodetector system of prism-coupling system 10 of FIG. 3A. In an example, ion-exchanged substrate 20 constitutes a chemically strengthened glass such as GORILLA® glass, made by Corning, Inc., of Corning, N.Y.

The system 10 includes a substrate holder 30 configured to hold substrate 20. In alternative embodiments, however, substrate holder 30 is not required. The system 10 also includes a coupling prism 40 that includes an input surface 42, an optional top flat surface 43, a coupling surface 44 and an output surface 46. The coupling prism 40 has a refractive index $n_p > n_0$. The coupling prism 40 is interfaced with substrate 20 by bringing coupling-prism coupling surface 44 and substrate top surface 22 into optical contact, thereby defining a substrate-prism interface ("interface") 50 that optionally includes an interfacing fluid (not shown).

The coupling prism 40 includes an output-side prism angle ("prism angle") α that measures the angle formed by output surface 46 and coupling surface 44. The selection of prism angle α is described in greater detail below.

With continuing reference to FIG. 3A, system 10 includes optical axes A1 and A2 that respectively pass through input and output surfaces 42 and 46 of coupling prism 40 to generally converge at interface 50 after accounting for refraction at the prism/air interfaces. The system 10 includes, in order along axis A1, a light source 60 that emits measuring light 62 of wavelength λ, an optional optical filter 66 that may be alternatively included in the detector path on axis A2, an optional light-scattering element 70 that forms scattered light 62S, and an optional focusing optical system 80 that may partially focus (measuring) light 62F, as explained below. Thus, in an example of system 10, there are no optical elements between light source 60 and prism input surface 42.

The system 10 also includes, in order along axis A2 from coupling prism 40, a collection optical system 90 having a focal plane 92 and a focal length f and that receives reflected light 62R as explained below, a polarizer system 100, and a photodetector system 130. The axis A1 defines the center of an optical path OP1 between light source 60 and coupling-prism coupling surface 44. The axis A2 defines the center of an optical path OP2 between coupling surface 44 and photo-detector system 130. Note that axes A1 and A2 may be bent at input and output surfaces 42 and 46, respectively, due to refraction. They may also be broken into sub-paths by the insertion of mirrors in optical paths OP1 and/or OP2.

In an example, photodetector system 130 includes a detector (camera) 110 and a frame grabber 120. In other embodiments discussed below, photodetector system 130 includes a CMOS or CCD camera. FIG. 3B is a close-up elevated view of polarizer system 100 and detector 110 of photodetector system 130. In an example, polarizer system 100 includes a TE polarizer section 100TE and a TM polarizer section 100TM. The photodetector system 130 includes a photosensitive surface 112. The photosensitive surface 112 resides in focal plane 92 of collection optical system 90, with the photosensitive surface being generally perpendicular to axis A2. This serves to convert the angular distribution of reflected light 62R exiting the coupling prism output surface 46 to a transverse spatial distribution of light at the sensor plane of camera 110. With reference to the close-up inset of FIG. 3B, in an example embodiment, photosensitive surface 112 comprises pixels 112p, i.e., detector 110 is a digital detector, such as a digital camera.

Splitting photosensitive surface 112 into TE and TM sections 112TE and 112TM allows for the simultaneous recording of digital images of the angular reflection spectra (mode spectra) for the TE and TM polarizations of reflected light 62R. This simultaneous detection eliminates a source of measurement noise that could arise from making the TE and TM measurements at different times, given that system parameters can drift with time.

In another embodiment of system 10, polarizer system 100 does not have a split polarizer configuration but instead comprises a single polarizer, rotated sequentially 90 degrees between two states that transmit the TM or the TE spectrum, to sequentially take the TM and TE coupling spectra. In this embodiment, polarizer system 100 can be placed in either light source path OP1 or detector path OP2.

Figure 3C:
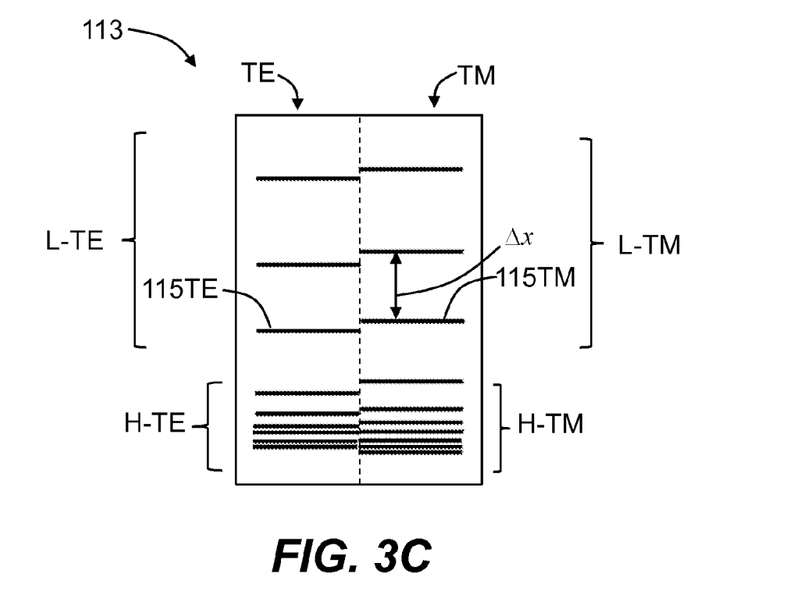
FIG. 3C is a schematic representation of TM and TE mode spectra as captured by the photodetector system of FIG. 3B.

FIG. 3C is a schematic representation of TM and TE mode spectra 113 as captured by photodetector system 130. The TM and TE mode spectra 113 are made up of respective spectral lines (mode lines) 115TM and 115TE. The TM and TE mode spectra each include lower-order modes (i.e., high-effective-index modes) L-TE and L-TM and higher-order modes (i.e., low-effective-index modes) H-TE and H-TM. The spacing between adjacent mode lines 115 is denoted Δx and varies along the length of the given mode spectrum 113, getting increasingly smaller from the lower-order modes to the higher-order modes.

Example light sources 60 include lasers, light-emitting diodes, and broader-bandwidth sources such as hot-filament lamps and quartz lamps. Example operating wavelengths λ of measuring light 62 generated by light source 60 can include near-ultra-violet, visible and infrared wavelengths. When light source 60 is coherent, the use of the aforementioned light-scattering element 70, which may be a moving or vibrating diffuser, can help mitigate speckle, which can be problematic for precise measurements of coupling spectra.

The system 10 includes a controller 150, which is configured to control the operation of the system. The controller 150 is also configured to receive and process image signals SI from photodetector system 130 that are representative of captured TE and TM mode spectra images. The controller 150 includes a processor 152 and a memory unit ("memory") 154. The controller 150 may control the activation and operation of light source 60 via a light-source control signal SL, and receives and processes image signals SI from photodetector system 130 (e.g., from frame grabber 120, as shown).

In an example, controller 150 comprises a computer and includes a reading device, for example, a floppy disk drive, a CD-ROM drive, a DVD drive, a magnetic optical disk (MOD) device (not shown) or any other digital device including a network-connecting device, such as an Ethernet device (not shown), for reading instructions and/or data from a computer-readable medium, such as a floppy disk, a CD-ROM, a DVD, a MOD, a flash drive or another digital source such as a network or the Internet. The controller 150 is configured to execute instructions stored in firmware and/or software (not shown), including signal-processing instructions for carrying out the surface birefringence/stress measurements disclosed herein. In examples, the terms "controller" and "computer" are interchangeable.

The controller 150 is programmable to perform the functions described herein, including the operation of system 10 and the post-processing (signal processing) of image signals SI to arrive at a measurement of a characteristic of substrate 20, such as the stress profile S(x), birefringence, or compressive stress CS, or the refractive index profile n(x), which may include TE and TM components. As used herein, the term "computer" is not limited to just those integrated circuits referred to in the art as computers but broadly refers to computers, processors, microcontrollers, microcomputers, programmable logic controllers, application-specific integrated circuits and other programmable circuits, and these terms are used interchangeably herein.

Software may implement or aid in the performance of the operations of system 10 disclosed herein, including the aforementioned signal processing. The software may be operably installed in controller 150 and in particular in processor 152 and memory 154. Software functionalities may involve programming, including executable code, and such functionalities may be used to implement the methods disclosed herein. Such software code is executable by the general-purpose computer or by the processor unit described below.

In operation, the code and possibly the associated data records are stored within a general-purpose computer platform, within processor 152 and/or in memory 154. At other times, however, the software may be stored at other locations and/or transported for loading into the appropriate general-purpose computer systems. Hence, the embodiments discussed herein involve one or more software products in the form of one or more modules of code carried out by at least one machine-readable medium. Execution of such code by processor 152 of computer system 150 or by the processor unit enables the platform to implement the catalog and/or software downloading functions in essentially the manner performed in the embodiments discussed and illustrated herein.

The controller 150 and/or processor 152 may each employ a computer-readable medium or machine-readable medium (e.g., memory 154), which refers to any medium that participates in providing instructions to the processor for execution, including, for example, determining an amount of surface birefringence/stress or the stress profile S(x) of substrate 20. The memory 154 constitutes a computer-readable medium. Such a medium may take many forms, including but not limited to non-volatile media, volatile media and transmission media. Non-volatile media include, for example, optical or magnetic disks, such as any of the storage devices in any computer(s) operating as one of the server platforms discussed above. Volatile media include dynamic memory, such as the main memory of such a computer platform. Physical transmission media include coaxial cables, copper wire and fiber optics, including the wires that comprise a bus within a computer system.

Common forms of computer-readable media therefore include, for example, a floppy disk, a flexible disk, a hard disk, magnetic tape, flash drives and any other magnetic medium; a CD-ROM, a DVD and any other optical medium; less commonly used media such as punch cards, paper tape and any other physical medium with patterns of holes; a RAM, a PROM, an EPROM, a FLASH-EPROM and any other memory chip or cartridge; a carrier wave transporting data or instructions, cables or links transporting such a carrier wave, or any other medium from which a computer can read programming code and/or data. Many of these forms of computer-readable media may be involved in carrying one or more sequences of one or more instructions to processor 152 for execution.

In an example, controller 150 is programmed to determine at least one characteristic of ion-exchanged substrate 10 based on the measured mode spectra. Example characteristics include: surface stress, stress profile, compressive stress, depth-of-layer, refractive index profile and birefringence. In an example, controller 150 is programmed to carry out calculations as disclosed in the article by A. Brandenburg, "Stress in Ion-Exchanged Glass Waveguides," *Journal of Lightwave Technology* 4, no. 10 (October 1986): 1580-93, and as also disclosed in the aforementioned '546 application.

The system 10 may be a modified version of a commercial prism-coupling instrument, such as the FSM-6000 prism-coupling instrument made and sold by Orihara Industrial Co., Ltd., of Tokyo, Japan. The FSM-6000 instrument represents the state of the art in high-throughput non-destructive measurements of stress in flat ion-exchanged glasses, and utilizes a coupling prism 40 with a prism index $n_p$=1.72 at 589 nm. The FSM-6000 uses an index-matching fluid having an index $n_f$=1.64. In the FSM-6000 instrument, the surface compressive stress (CS) is calculated from the effective indices $n_{eff}$ of the first two transverse magnetic (TM) and the first two transverse electric (TE) modes, while the total number of observed modes is used along with the substrate index and the aforementioned effective indices of the first two modes for the depth-of-layer (DOL) calculation based on a linear refractive-index profile assumption.

Coupling Prism

Figure 4:
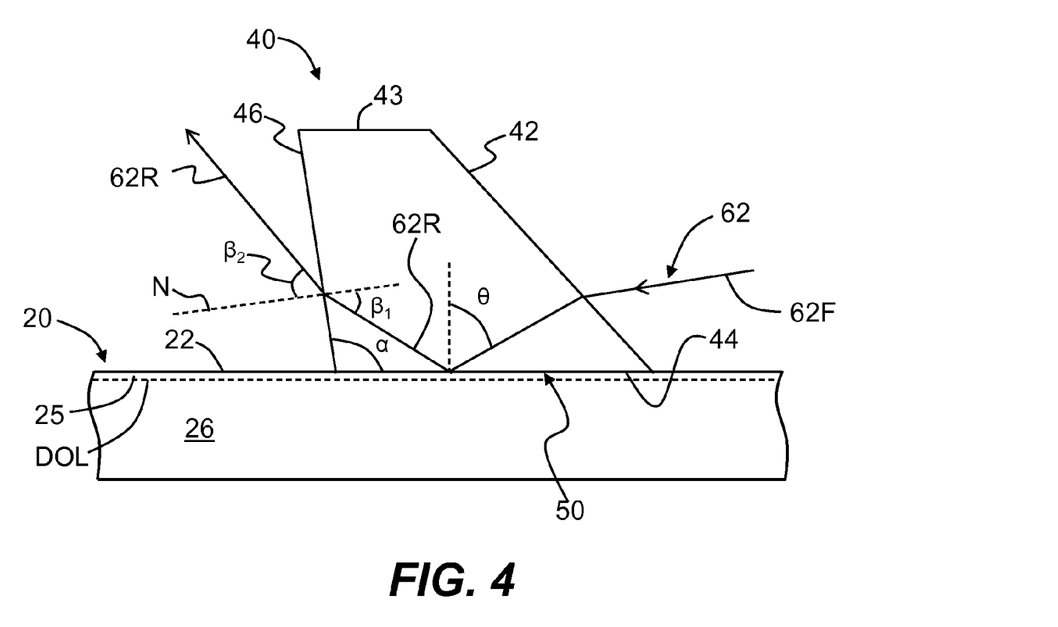
FIG. 4 is a close-up view of the prism-coupling system showing an example coupling prism as disclosed herein, with the coupling prism interfaced with the ion-exchanged substrate and the waveguide formed therein.

FIG. 4 is a close-up side view of coupling prism 40 shown interfaced with top surface 22 of ion-exchanged substrate 20, along with the path of an example light ray 62 that starts out as focused light 62F that passes through input surface 42, reflects from coupling surface 44 at angle θ as reflected light 62R with the incident angle $\beta_1$ with respect to the normal of the prism output surface 46, and exits the output surface as the reflected light with exit angle $\beta_2$.

For a given waveguide mode, the incident resonance angle with respect to the normal of the coupling facet of the prism is given by:

$$\sin(\theta) = \frac{n_{eff}}{n_p} \tag{1}$$

where $n_p$ is the refractive index of the prism and $n_{eff}$ is the effective index of the waveguide mode. The relationship between corresponding incident and exit angles $\beta_1$ and $\beta_2$ with respect to the normal N of output surface 46 of coupling prism 40 is:

$$n_p \sin(\beta_1) = n_{air} \sin(\beta_2) \tag{2}$$

where $n_{air}$=1 is the refractive index of the air.

The relationship between the magnitude of the incident angle $\beta_1$ and the prism angle α relative to angle θ is given by:

$$\beta_1 = \theta - \alpha, \text{ when } \alpha \leq 90°, \tag{3a}$$

$$\beta_1 = \alpha - \theta, \text{ when } \alpha > 90°. \tag{3b}$$

From Equations (1) and (2), the relationship between the exit angle $\beta_2$ as a function of the prism angle α and the effective index $n_{eff}$ is written as:

$$\beta_2 = \cos^{-1} \sqrt{\frac{1 + n_{eff} \sqrt{n_p^2 - n_{eff}^2} \sin(2\alpha) - }{n_{eff}^2 \cos^2 a - (n_p^2 - n_{eff}^2)\sin^2 \alpha}} \tag{4}$$

Then, the sensitivity of prism exit angle $\beta_2$ relative to the corresponding effective index $n_{eff}$ is expressed as:

$$\frac{d\beta_2}{dn_{eff}} = \frac{\cos\alpha + \frac{n_{eff}}{\sqrt{n_p^2 - n_{eff}^2}}\sin\alpha}{\sqrt{1 + n_{eff}\sqrt{n_p^2 - n_{eff}^2}\sin(2\alpha) - n_{eff}^2 \cos^2\alpha - (n_p^2 - n_{eff}^2)\sin^2\alpha}} \tag{5}$$

When photodetector system 130 is arranged relative to collection optical system 90 such that axis A2 is approximately perpendicular to focal plane 92 of camera 110, the spacing Δx between two (vertical) mode lines 115 having a difference $\Delta\beta_2$ in the exit angle $\beta_2$ is given by:

$$\Delta x = f[\tan(\beta_2 + \Delta\beta_2) - \tan(\beta_2)] \approx f\Delta\beta_2 = f\frac{d\beta_2}{dn_{eff}}\Delta n_{eff} \tag{6}$$

To capture with photodetector system 130 the entire spectrum of all the modes supported by ion-exchanged substrate 20, the prism angle α must be smaller than the angle for which the exit angle $\beta_2$=90 for effective index $n_{eff}$ is equal to or slightly larger than the refractive index $n_s$ of the substrate 20. This translates to the following condition on the maximum prism angle $\alpha_{max}$:

$$\alpha_{max} = \arcsin\left(\frac{n_s}{n_p}\right) + \arcsin\left(\frac{1}{n_p}\right) \tag{7}$$

The minimum prism angle $\alpha_{min}$ that allows for the capture of the entire mode spectrum by photodetector system 130 is dictated by the condition $\beta_2 \leq 90°$ when $n_{eff}$ equals or is slightly smaller than the refractive index $n_0$ of substrate surface 22, and is given by:

$$\alpha_{min} = \arcsin\left(\frac{n_0}{n_p}\right) - \arcsin\left(\frac{1}{n_p}\right) \tag{8}$$

Therefore, to capture the entire spectrum of all the modes in a waveguide, the prism angle α must be in the range $\alpha_{max} \geq \alpha \geq \alpha_{min}$.

The Optimum Prism Angle

The conventional wisdom of prism-coupling systems is to employ a coupling prism (often an isosceles) wherein the prism angle α between the coupling surface and the exit surface is most often equal to or nearly 60°, and generally less than 75°. Prism angles as high as 75° have been used in rare cases when the prism refractive index is only slightly larger (2%-4% larger) than the index of the measured glass substrate. Such prisms have had small dimensions (<8 mm) due to small coupling lengths and would not be adequate for resolving the spectra of DIOX profiles with large DOL. The typical prism angle results in a sensitivity of exit angle to effective index $n_{eff}$, expressed as $d\beta_2/dn_{eff}$, that increases with increasing $n_{eff}$. While in the past this has not been problematic, it turns out that this sensitivity is undesirable when measuring a waveguide with a large DOL that exhibits sparsely spaced lower-order modes associated with higher effective indices $n_{eff}$ and densely spaced higher-order modes associated with lower effective indices.

Figure 5A:
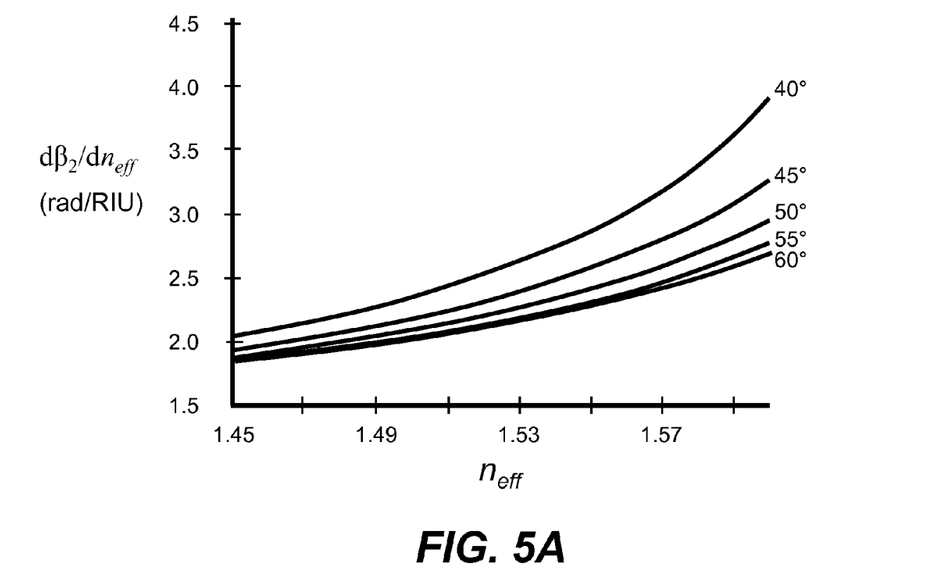
FIGS. 5A and 5B are plots of $d\beta_2/dn_{eff}$ (radians/RIU) versus $n_{eff}$ for prism angles $\alpha$ of 40°, 45°, 50°, 55° and 60° (FIG. 5A), and for prism angles $\alpha$ of 60°, 74°, 82°, 86°, 88°, 90° and 92° (FIG. 5B), based on a prism index $n_p$=1.7298.
Figure 5B:
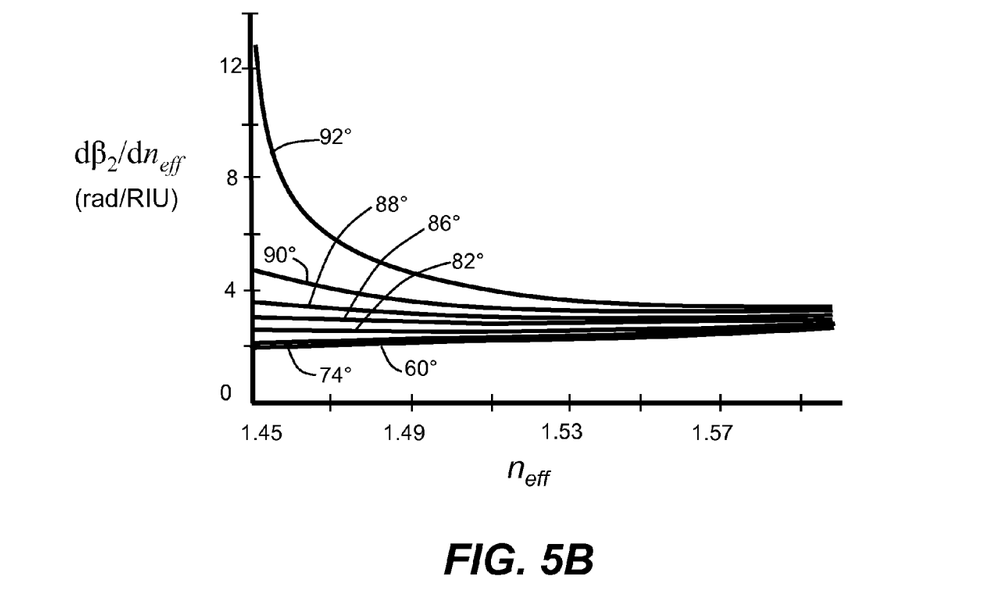

FIGS. 5A and 5B are plots of the sensitivity of prism exit angle $\beta_2$ relative to effective index $n_{eff}$ as a function of effective index $n_{eff}$, $d\beta_2/dn_{eff}$ (radians/RIU) versus $n_{eff}$ for prism angles α of 40°, 45°, 50°, 55° and 60° (FIG. 5A) and for prism angles α of 60°, 74°, 82°, 86°, 88°, 90° and 92° (FIG. 5B) based on a prism index $n_p$=1.7298. Note that FIG. 5A has a smaller range for $d\beta_2/dn_{eff}$ than does FIG. 5B. The curve for a prism angle α=60° of FIG. 5A shows a positive slope and a low rate of change over the range of $n_{eff}$. While this allows for measuring waveguides with various refractive indices, the positive slope of the curve of $d\beta_2/dn_{eff}$ is problematic for measuring waveguides with a steep profile and large index difference, or waveguides having a deep profile portion, such as the profile of a DIOX glass, formed, for example, by $Ag^+$ and $K^+$ diffusions.

The positive slope of $d\beta_2/dn_{eff}$ versus $n_{eff}$ supports a relatively wide spacing between lines of low-order modes (or high effective index) and a very narrow spacing between lines of high-order modes (or low effective index) in the images of the TE and TM mode spectra (see FIG. 3C). This leads to two major measurement problems. The first is that the narrow line spacing of the high-order modes limits the ability to resolve such lines using an industrial high-resolution sensor of moderate cost, which limits the measurable DOL. The second is that the wide spacing of the high-order modes reduces the measurement dynamic range, thus preventing the use of a collection optical system 90 having a longer focus length to improve measurement accuracy and sensitivity for the deep portion of the index or stress profile.

FIGS. 5A and 5B show that the slope of the $d\beta_2/dn_{eff}$ curve changes from negative to positive when the prism angle α is larger than about 86°. As the prism angle α increases, the exit angle sensitivity $d\beta_2/dn_{eff}$ in the low range of $n_{eff}$ (1.45 to 1.5) grows rapidly, while the sensitivity in the high range of $n_{eff}$ (1.5 to 1.6) changes more slowly. This character is exactly what is needed for mitigating the aforementioned two measurement problems since it significantly enlarges the line spacing Δx between mode lines 115 in the low range of $n_{eff}$ without significantly changing the mode-line spacing Δx between modes in the high range of $n_{eff}$.

The physical effect that enables such relative increase for the low $n_{eff}$ range is the substantial refraction for incident angles $\beta_1$ as they approach the critical angle for total internal reflection. This effect benefits the sensitivity of low-index modes when their incident angles $\beta_1$ at output surface 46 are larger than the incident angles of low-order modes that have higher effective indices $n_{eff}$. The improvement of the sensitivity of prism angle α as a function of $n_{eff}$ when the prism angle is changed from 60° to 92° is about 600% for $n_{eff}$=1.45. This means that line spacing between modes is enlarged by about six times for an effective index of 1.45. On the other hand, the change of the sensitivity is only about 27% for the highest effective index $n_{eff}$=1.6. The large improvement in sensitivity could be pushed to higher effective index values beyond $n_{eff}$=1.45, such as 1.5, by selecting a higher prism index $n_p$, e.g., $n_p$=1.8.

As indicated by Equation (6) above, the spacing Δx between modes (mode lines 115) as measured at photodetector system 130 is proportional to the distance between collection optical system 90 and detector 110, which is approximately equal to the focal length of the collection optical system, and to the sensitivity of exit angle $\beta_2$ to the mode effective index $n_{eff}$. To capture the entire mode spectrum, its spatial extent must be no greater than the size of photosensitive surface 112. An example detector used in system 10 has a photosensitive surface 112 with a width of 22.3 mm. Therefore, when the $d\beta_2/dn_{eff}$ sensitivity is increased, it may be necessary to configure collection optical system 90 with a different focal length to ensure that the image size of the mode spectrum remains substantially the same. On the other hand, one can compare the change of the line spacing between mode lines 115 for various combinations of coupling prism 40 and collection optical system 90 to identify those combinations that produce substantially identical image sizes.

Figure 6:
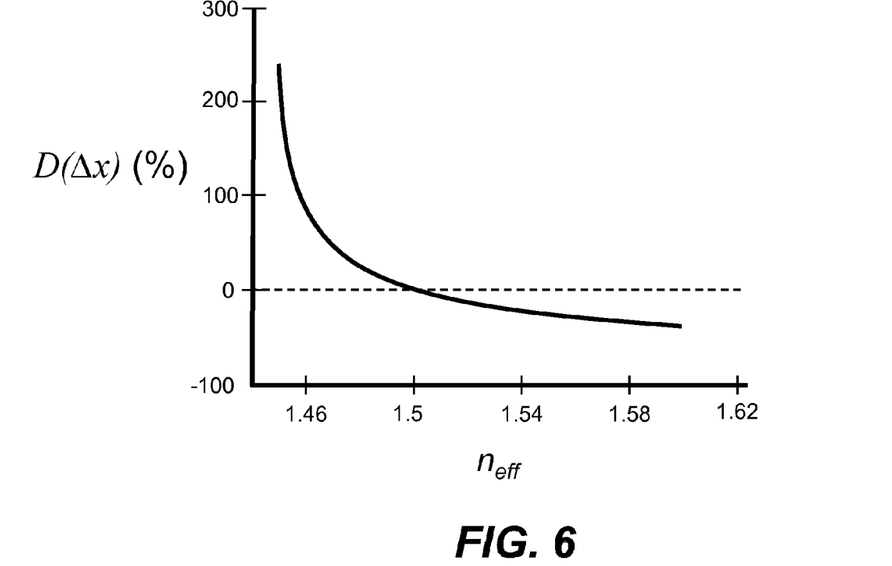
FIG. 6 is a plot of the change $D(\Delta x)$ (%) in the mode-line spacing $\Delta x$ at the focal plane of the collection optical system versus the effective index $n_{eff}$ for a prism angle $\alpha$=92.0° relative to a prism angle of 60° while keeping the overall width of the mode-spectrum image the same size, with the dashed horizontal line at $D(\Delta x)$=0.

FIG. 6 is a plot of the change D(Δx) in the spacing Δx between adjacent modes lines (%) at focal plane 92 of collection optical system 90 versus the effective index $n_{eff}$ for a prism angle α=92°, while keeping the width of the mode-spectrum image the same compared with a prism with an exit angle α=60°. The dashed horizontal line in the plot indicates the transition between where the mode-line spacing increases or decreases, i.e., where no change in the mode-line spacing occurs. The focal length of collection optical system 90 is 130 mm for α=60° and is changed to 63.3 mm for α=92°. The plot of FIG. 6 shows that the line spacing x between adjacent modes in the low range of $n_{eff}$ (<1.5) is increased by increasing the prism angle α from 60° to 92°. On the other hand, in the high range of $n_{eff}$ (>1.5), the line spacing x between mode lines 115 is reduced by changing the prism angle α from 60° to 92°, thereby enhancing the favorable tradeoff between the improvement of the sensitivity and dynamic range.

This feature is particularly useful for measuring DIOX substrates 20 since the mode-line spacing x is much larger in the high effective index range than in the low effective index range. Thus, the prism angle α can be selected such that the more spaced-apart mode lines 115 can be spatially compressed while the more tightly packed mode lines can be spatially decompressed (i.e., spread apart). This compression and decompression of the mode-line spacing is due to the different refraction angles of reflected light 62R for the different mode lines 115 when exiting coupling prism 40 at output surface 46.

This compression and decompression by definition alters (distorts, adjusts, etc.) the actual or true mode spectra and needs to be corrected (re-adjusted, undistorted, etc.) after mode lines 115 are detected by detector 110. While this correction adds a step to the measurement and characterization processes, the alteration of the mode spectra due to the selective compression and decompression of mode lines 115 allows for the mode spectrum (or spectra) to fit within detector 110 in a manner that provides enough detector pixels 112p to adequately sample all the detected mode lines. It provides for efficient use of the existing detector size and obviates the need to increase the detector size (which usually means purchasing a larger and more expensive detector 110) to obtain adequate spatial sampling of the mode spectrum or spectra, and the use of a larger and more expensive optical system to collect whole spectrum light.

As shown in FIGS. 5A and 5B, it can be seen that the larger the prism angle $\alpha$, the better the improvement in sensitivity for the low effective index range. However, to capture the entire spectrum of all modes, the prism angle $\alpha$ must be smaller than the maximum prism angle $\alpha_{max}$ as defined above. The maximum prism angle $\alpha_{max}$ depends on the prism refractive index $n_p$ and the refractive index $n_s$ of substrate 20.

Figure 7:
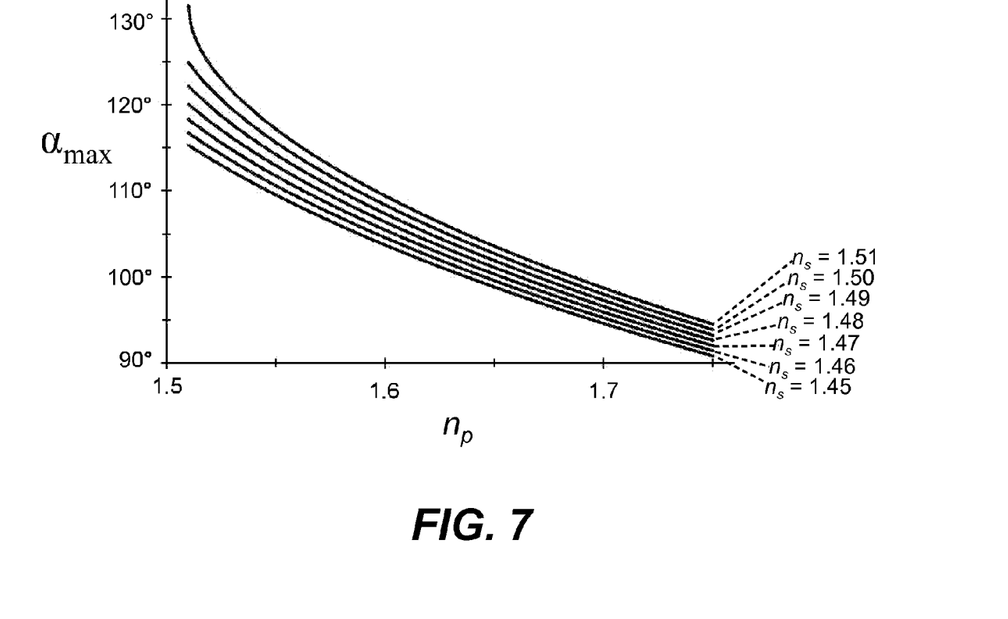
FIG. 7 plots the maximum prism angle $\alpha_{max}$ versus the prism refractive index $n_p$ for substrate bulk refractive indices $n_s$=1.45, 1.46, 1.47, 1.48, 1.49, 1.50 and 1.51.
Figure 8:
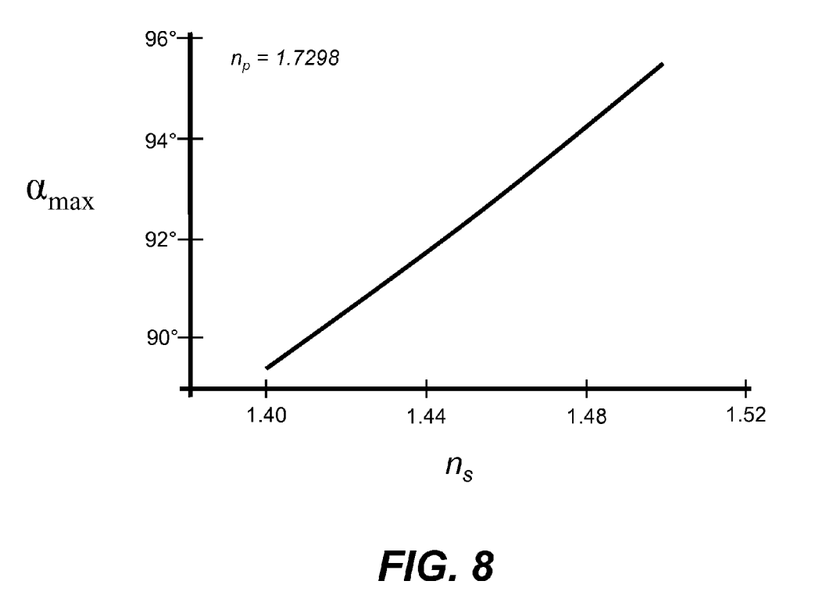
FIG. 8 plots the maximum prism angle $\alpha_{max}$ versus the substrate bulk refractive index $n_s$ for a prism refractive index $n_p$=1.7298.

FIG. 7 plots the maximum prism angle $\alpha_{max}$ versus the prism refractive index $n_p$ for substrate refractive indices $n_s$=1.45, 1.46, 1.47, 1.48, 1.49, 1.50 and 1.51. FIG. 8 plots the maximum prism angle $\alpha_{max}$ versus the substrate refractive index $n_s$ for a prism refractive index $n_p$=1.7298. It can be seen that the maximum prism angle $\alpha_{max}$ almost linearly increases with the refractive index $n_s$ of substrate 20.

When reflected light 62R is incident at output surface 46 from within coupling prism 40 at large incidence angles $\beta_1$ that are near the critical angle, there can be a large difference in reflectivity between the TM and TE polarizations. This can cause some practical issues when the TM and TE mode spectra are captured simultaneously, such as illustrated in FIG. 3B. In particular, the TE mode spectrum may have substantially less light reaching detector 110. Thus, in an example embodiment, output surface 46 includes an anti-reflection coating optimized for the range of incidence angles $\beta_1$ characteristic of the desired range of effective indices $n_{eff}$ to be measured.

In an example, the prism angle $\alpha$ is selected to be slightly smaller than the maximum prism angle $\alpha_{max}$. In various examples, the prism angle $\alpha$ is in the range $0.81\alpha_{max} \leq \alpha \leq 0.99\alpha_{max}$, or in the range $0.90\alpha_{max} \leq \alpha \leq 0.99\alpha_{max}$, or in the range $0.95\alpha_{max} \leq \alpha \leq 0.99\alpha_{max}$.

Once a measurement of the mode spectrum is made using system 10 with coupling prism 40 having the selected prism angle $\alpha$ per above, controller 150 is used to post-process the measured mode spectrum. This is because the mode spectrum is "distorted" by virtue of the different mode lines 115 having different output angles $\beta 2$. Said differently, the spacing between adjacent modes is affected in a non-linear way, as defined by $d\beta_2/dn_{eff}$ given in Equation (5) and as illustrated in FIG. 5. Fortunately, the "distortion" or selective adjustment of the mode spectrum is well-defined and known based on the particular operating parameters of system 10, and so can be corrected by post-processing of the measured spectra using controller 150. Equations (5-6) can be used by controller 150 to do post-processing correction and Equation (6) can be used by controller 150 to establish the proper spacing $\Delta n_{eff\text{-}}$ between adjacent modes for the TE and TM mode spectra. In an alternative embodiment, $n_{eff}$ is directly calculated from the positions x on the sensor using an exact formula disclosed in the aforementioned '377 publication.

An effective index is assigned corresponding to the x coordinate of the center of the image, $x_{center}$. Then the exit angle corresponding to that center index is found through the relation:

$$\beta_2^{center} = \sin^{-1}\left(n_p \sin\left(\sin^{-1}\left(\frac{n_{center}}{n_p}\right) - \alpha\right)\right) \quad (9)$$

Using the above relation, the effective index corresponding to any position x on the sensor can be found via the following exact relationship:

$$n_{eff}(x) = \sin\left\{\alpha + \sin^{-1}\left[\frac{1}{n_p}\sin\left(\beta_2^{center} + \tan^{-1}\left(\frac{x - x_{center}}{f}\right)\right)\right]\right\} \quad (10)$$

The controller 150 then proceeds to calculate at least one of the aforementioned characteristics of DIOX substrate 20 using calculations known in the art.

Figure 9A:
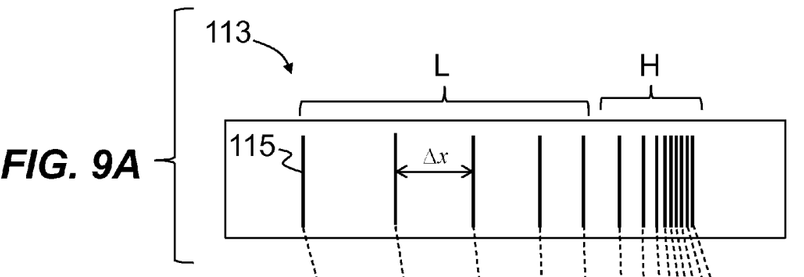
FIG. 9A is a schematic diagram that illustrates an example ideal, pure, undistorted or otherwise unaltered mode spectrum that has mode lines with respective mode-line spacings $\Delta x$.

FIG. 9A is a schematic diagram that illustrates an example ideal, pure, undistorted (when $d\beta_2/dn_{eff}$ is approximately constant over the angular range of the measurement) or otherwise unaltered mode spectrum 113 that has mode lines 115 with respective mode-line spacings $\Delta x$, which as discussed above vary as a function of mode order. This ideal mode spectrum 113 exists at the substrate-prism interface 50 but is not readily accessible and so is generally not directly measurable.

Figure 9B:
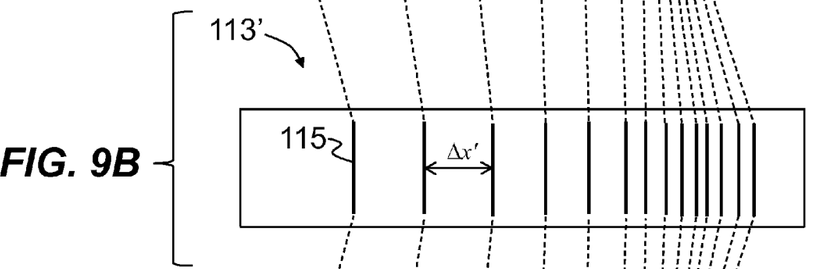
FIG. 9B is similar to FIG. 9A but wherein the mode spectrum is an adjusted version of mode spectrum of FIG. 9A, wherein the mode-line spacings have changed due to refraction at the output surface of the coupling prism and are defined by $\Delta x'$, as indicated by the dashed lines that connect the corresponding mode lines of FIGS. 9A and 9B.

FIG. 9B is similar to FIG. 9A and shows a mode spectrum 113' as an adjusted version of mode spectrum 113. In adjusted mode spectrum 113', the mode-line spacings have changed and are defined by $\Delta x'$, as indicated by the dashed lines that connect the corresponding mode lines 115. The change in the mode-line spacings arise, as discussed above, by virtue of the refraction at output surface 46 of reflected light 62R associated with the different modes of the mode spectrum. Note how the adjusted mode-line spacings $\Delta x'$ of the more spaced-apart lower-order modes L in mode spectrum 113' have decreased as compared to the ideal mode spectrum 113, while the mode-line spacings of the more tightly spaced higher-order modes H has increased as compared to the ideal mode spectrum. Note also that in the example, the overall size of the adjusted mode spectrum 113' is about the same as that of the ideal mode spectrum 113 of FIG. 9A.

Figure 9C:
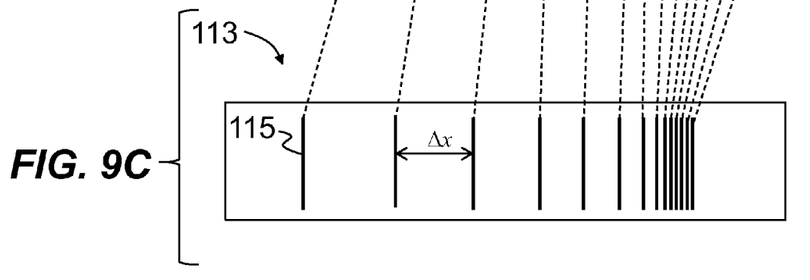
FIG. 9C shows the correction (or re-adjustment) made to the adjusted version of mode spectrum of FIG. 9B to obtain the corrected (unadjusted) mode spectrum of FIG. 9A.

FIG. 9C shows the correction (or re-adjustment) made to the adjusted version of mode spectrum 113' to obtain the corrected (unadjusted) mode spectrum 113 of FIG. 9A, which was assumed to be previously unknown. This correction is accomplished by knowing the configuration of system 10, including that of coupling prism 40, and how the refraction at output surface 46 of the coupling prism impacts the path of measuring light 62 associated with the different mode lines 115 for the different modes of the original or true mode spectrum 113. As discussed above, Equations (5-6) provide the relationship between the change in the mode-line spacing $\Delta x$ as a function of effective index $n_{eff}$. Thus, controller 150 can be used to obtain the true or unadjusted mode spectrum 113 via implementation of Equation (6) in a computer-readable medium (e.g., software).

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A measurement system for measuring at least one mode spectrum of a waveguide formed in a top surface of a substrate and having a depth-of-layer (DOL) of greater than 50 microns, the system comprising:
    a coupling prism having an input surface, an output surface and a coupling surface, a refractive index $n_p$, and a prism angle $\alpha$ between the output surface and the coupling surface, and wherein the coupling surface interfaces with the waveguide at the substrate top surface, thereby defining a substrate-prism interface;
    a light source system configured to illuminate the substrate-prism interface through the input surface of the prism, thereby forming reflected light that includes mode lines of the at least one mode spectrum having a first size, wherein the reflected light exits the output surface of the coupling prism;

a photodetector system having a detector and arranged to receive the reflected light from the coupling prism and detect the at least one mode spectrum on the detector; and a controller configured to process the detected at least one mode spectrum to correct a distortion of the mode lines caused by refraction of the reflected light at the output surface of the coupling prism to a corrected mode spectrum having a second size; and wherein the coupling prism has a maximum prism angle $\alpha_{max}$ equal to the critical angle at greater than which the reflected light is totally internally reflected at the output surface of the prism, and wherein the prism angle $\alpha$ is in the range $0.81\alpha_{max} \leq \alpha \leq 0.99\alpha_{max}$, and wherein the first size is substantially the same as the second size.

2. The measurement system according to claim 1, wherein the prism angle $\alpha$ is in the range $0.90\alpha_{max} \leq \alpha \leq 0.99\alpha_{max}$.

3. The measurement system according to claim 2, wherein the prism angle $\alpha$ is in the range $0.95\alpha_{max} \leq \alpha \leq 0.99\alpha_{max}$.

4. The measurement system according to claim 1, wherein the at least one mode spectrum includes a TE mode spectrum and a TM mode spectrum.

5. The measurement system according to claim 1, wherein the detector includes a first section that detects the TE mode spectrum and a second section that detects the TM mode spectrum.

6. The measurement system according to claim 1, wherein the prism angle $\alpha$ is greater than 90°.

7. The measurement system according to claim 1, wherein the coupling prism has a flat top surface.

8. A method of measuring mode spectra of a waveguide formed in a top surface of a substrate having a depth-of-layer (DOL) greater than 50 μm, comprising:

interfacing a coupling prism with the substrate to form a substrate-prism interface, the coupling prism having a coupling prism angle defined by an output surface and that is in the range $0.81\alpha_{max} \leq \alpha \leq 0.99\alpha_{max}$, wherein $\alpha_{max}$ defines a maximum coupling prism angle associated with total internal reflection occurring within the coupling prism;

directing light through the coupling prism to the substrate-prism interface to form reflected light that mode lines of at least one mode spectrum of the waveguide, wherein the reflected light exits the output surface of the coupling prism;

detecting the mode lines of the at least one mode spectrum of the reflected light that exits the coupling prism, wherein the mode lines have an adjusted mode-line spacing due to refraction of the reflected light at the output surface of the coupling prism; and correcting the adjusted mode-line spacing after said detecting.

9. The method according to claim 8, wherein the prism angle $\alpha$ is in the range $0.90\alpha_{max} \leq \alpha \leq 0.99\alpha_{max}$.

10. The method according to claim 9, wherein the prism angle $\alpha$ is in the range $0.95\alpha_{max} \leq \alpha \leq 0.99\alpha_{max}$.

11. The method according to claim 8, wherein the prism angle $\alpha$ is greater than 90°.

12. The method according to claim 8, further including determining at least one characteristic of the waveguide based on the corrected mode-line spacing.

13. The method according to claim 12, wherein the at least one characteristic of the waveguide includes one or more of: surface stress, stress profile, compressive stress, the DOL, refractive index profile and birefringence.

14. The method according to claim 8, wherein the at least one mode spectrum has a first size, and wherein said correcting the adjusted mode-line spacing after said detecting forms an adjusted mode spectrum having a second size that is substantially the same as the first size.

15. The method according to claim 8, wherein the at least one mode spectrum consists of a TE mode spectrum and a TM mode spectrum.

16. The method according to claim 8, including forming waveguide by a double ion-diffusion (DIOX) process.

17. A method of measuring mode spectra of a waveguide formed in a top surface of a substrate by double ion diffusion to a depth-of-layer (DOL) greater than 50 μm, comprising:

interfacing a coupling prism with the waveguide, the coupling prism having an input surface, an output surface, a coupling surface that interfaces the top surface to define a substrate-prism interface, the coupling prism having a coupling prism angle $\alpha$ defined by the coupling surface and the output surface, and a maximum prism angle $\alpha_{max}$ that corresponds to a total-internal-reflection angle at the output surface, wherein the coupling prism angle is in the range $0.81\alpha_{max} \leq \alpha \leq 0.99\alpha_{max}$;

directing light through the input surface to the substrate-prism interface, thereby forming reflected light that includes higher-order and lower-order mode lines of the mode spectra, wherein the reflected light exits the coupling prism at the output surface and is made incident upon a detector;

detecting with the detector the higher-order and lower-order mode lines of the mode spectra, wherein the mode lines have an adjusted mode spacing due to refraction of the reflected light at the output surface of the coupling prism; and after said detecting, correcting the adjustment in the mode-line spacing.

18. The method according to claim 17, further including determining at least one characteristic of the waveguide based on the corrected mode-line spacing.

19. The method according to claim 18, wherein the at least one characteristic of the waveguide includes one or more of: surface stress, stress profile, compressive stress, the DOL, refractive index profile and birefringence.

20. The method according to claim 17, wherein the coupling prism angle $\alpha$ is in the range $0.90\alpha_{max} \leq \alpha \leq 0.99\alpha_{max}$.

\* \* \* \* \*